US009486259B2

(12) United States Patent
Mohamed et al.

(10) Patent No.: US 9,486,259 B2
(45) Date of Patent: Nov. 8, 2016

(54) BONE FIXATION DEVICE

(71) Applicants: Hossam Abdel Salam El Sayad Mohamed, Ontario (CA); Houda Abdulrahman M. Al Mansour, Ontario (CA)

(72) Inventors: Hossam Abdel Salam El Sayad Mohamed, Ontario (CA); Houda Abdulrahman M. Al Mansour, Ontario (CA)

( * ) Notice: Subject to any disclaimer, the term of this patent is extended or adjusted under 35 U.S.C. 154(b) by 468 days.

(21) Appl. No.: 13/995,754

(22) PCT Filed: Jan. 28, 2013

(86) PCT No.: PCT/IB2013/000100
§ 371 (c)(1),
(2) Date: Jun. 19, 2013

(87) PCT Pub. No.: WO2014/114968
PCT Pub. Date: Jul. 31, 2014

(65) Prior Publication Data
US 2014/0378974 A1    Dec. 25, 2014

(51) Int. Cl.
*A61B 17/76* (2006.01)
*A61B 17/74* (2006.01)
*A61B 17/86* (2006.01)

(52) U.S. Cl.
CPC ........... *A61B 17/742* (2013.01); *A61B 17/746* (2013.01); *A61B 17/8685* (2013.01)

(58) Field of Classification Search
CPC .. A61B 17/74; A61B 17/742; A61B 17/746; A61B 17/8685
USPC ................................ 606/66, 86–89
See application file for complete search history.

(56) References Cited

U.S. PATENT DOCUMENTS 3,002,514 A * 10/1961 Deyerle ............... A61B 17/746
606/67
4,432,358 A * 2/1984 Fixel .................... A61B 17/742
606/66

(Continued)

FOREIGN PATENT DOCUMENTS

EP     2108322 A1    10/2009
WO    98/02105 A1     1/1998

OTHER PUBLICATIONS

International Search Report for PCT/IB2013/000100 mailed Sep. 23, 2013.

*Primary Examiner* — Jan Christopher Merene
*Assistant Examiner* — Atiya Mahmud
(74) *Attorney, Agent, or Firm* — Caesar Rivise, PC

(57) ABSTRACT

A bone fixation device for repairing a fracture of the proximal femur is disclosed. It includes a jack tube, a compression screw and a nail. The jack tube is an elongated tubular member having a base plate and a side wall defining central passageway. The base plate is arranged to be secured to the femur by screws. The side wall of jack tube includes plural longitudinally extending slots. The nail is a tubular member having plural linear blades located in respective slots in the jack tube and plural spikes extending out of the distal end of the nail. The compression screw is arranged to be disposed within the nail to form a slidable unit and has internal threads to engage threads in the jack tube so that rotation of the compression screw slides the nail down the jack tube, with the blades and spikes digging into the surrounding bone.

16 Claims, 2 Drawing Sheets

(56) References Cited

U.S. PATENT DOCUMENTS

| | | | | |
|---|---|---|---|---|
| 4,657,001 A * | 4/1987 | Fixel | ................... | A61B 17/74 606/66 |
| 5,087,260 A * | 2/1992 | Fixel | ................... | A61B 17/746 606/282 |
| 6,780,185 B2 | 8/2004 | Frei et al. | | |
| 7,118,572 B2 | 10/2006 | Bramlet et al. | | |
| 7,918,853 B2 * | 4/2011 | Watanabe | ............ | A61B 17/164 606/62 |
| 2007/0173838 A1 * | 7/2007 | Li | ........................ | A61B 17/746 606/67 |
| 2007/0270848 A1 * | 11/2007 | Lin | ...................... | A61B 17/746 606/65 |
| 2008/0140077 A1 * | 6/2008 | Kebaish | ............... | A61B 17/744 606/64 |

* cited by examiner

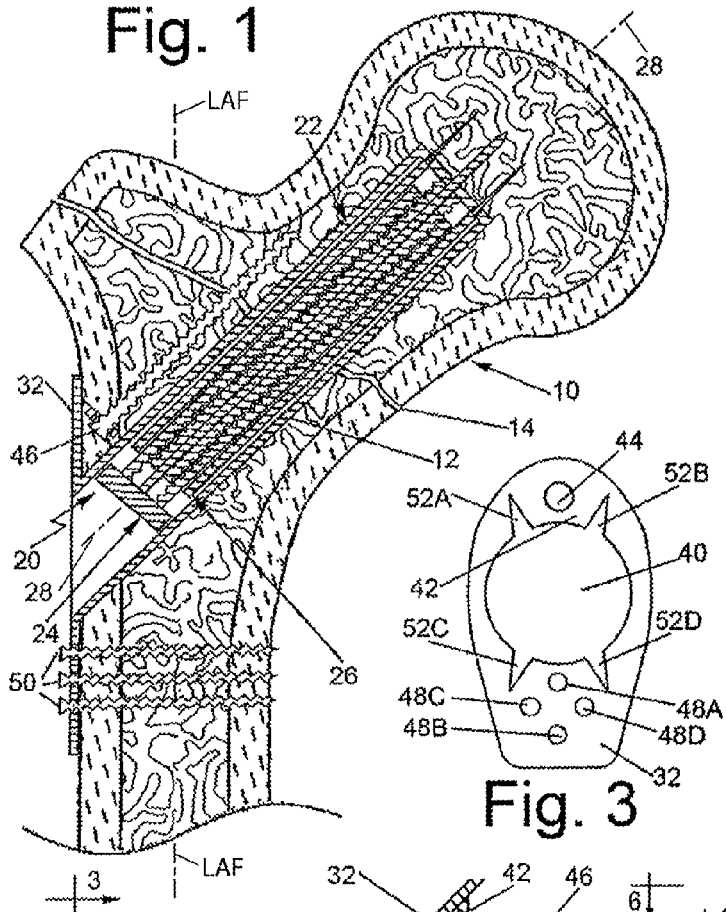
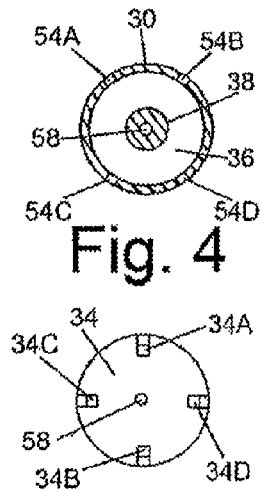
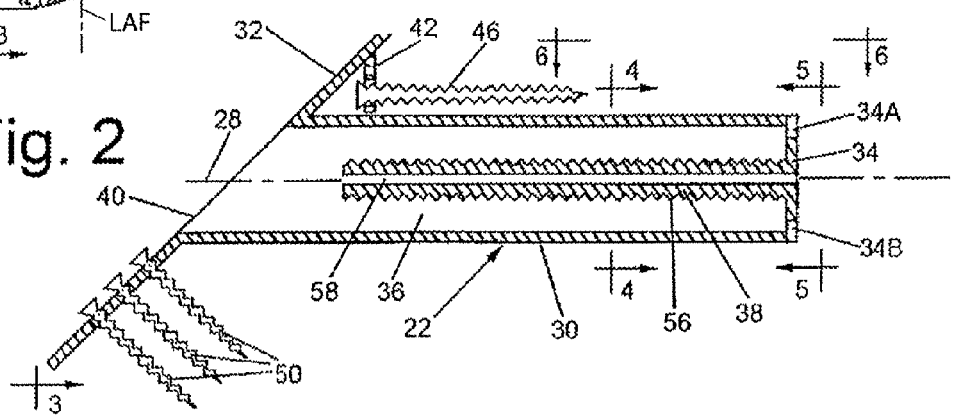

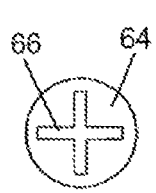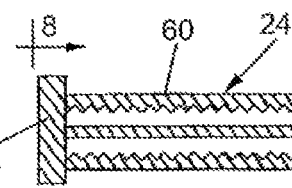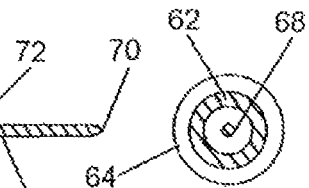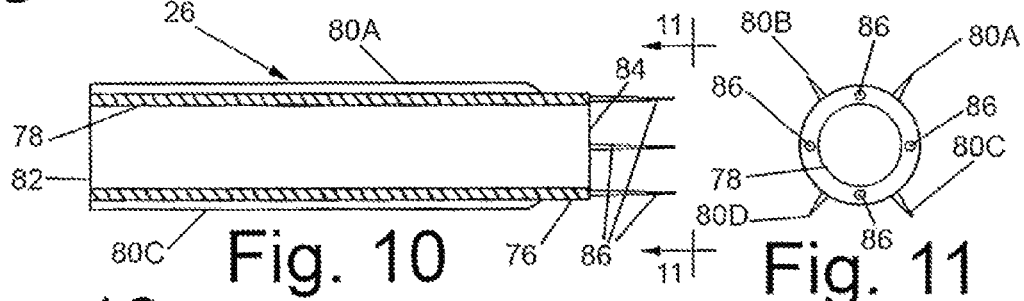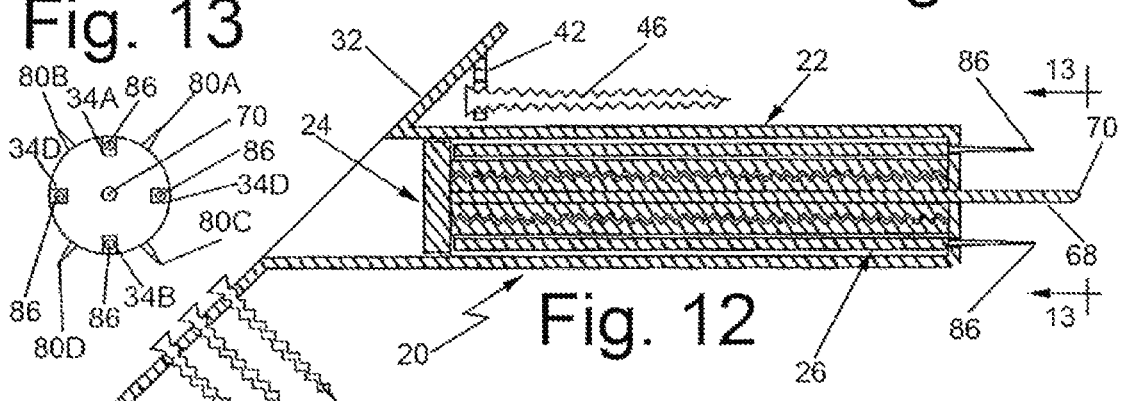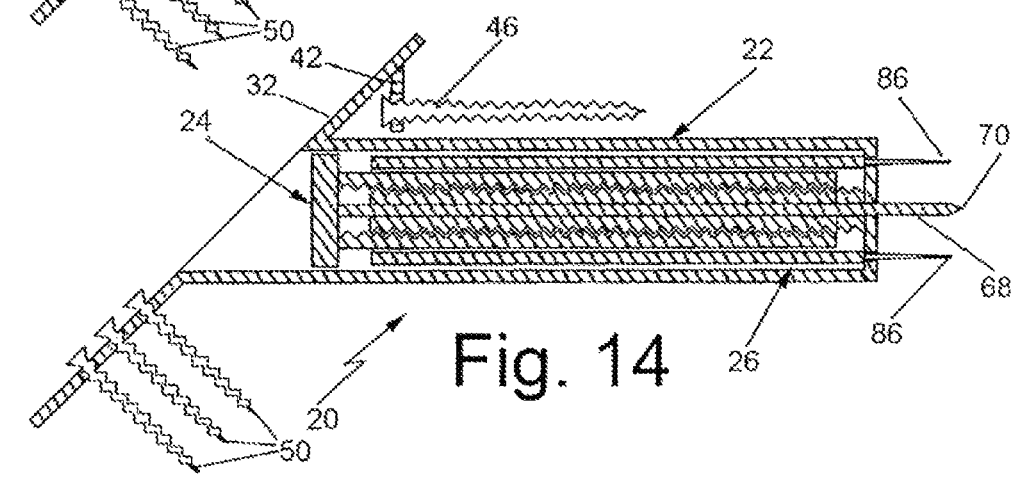

BONE FIXATION DEVICE

CROSS-REFERENCE TO RELATED APPLICATIONS

N/A

FIELD OF THE INVENTION

This invention relates generally to bone fixation devices and more particularly to devices for fixing fractures of the proximal femur of a patient.

BACKGROUND OF THE INVENTION

Various bone fixation devices are currently available for fixing fractures of the proximal femur, e.g., fractures of the femoral neck, and other proximal femoral fractures. For example, Zimmer, Inc. offers a Dynamic Hip Screw Plate System (referred to hereinafter as the "DHS system") which includes a threaded hip screw, a screw plate and a compression screw. The hip screw is inserted into an angularly extending bore (in the anterior-posterior view) in the proximal femur. The bore is formed by means of a reamer that is guided along the bore's desired path by a guide-wire. After the hip screw is in place in the bore the screw plate is mounted to the hip screw and secured to the femur by at least one (and likely several cortical screws). To that end the screw plate includes a barrel portion for coupling to the hip screw and an angularly extending portion for disposition alongside the contiguous portion of the femur. The angularly extending portion includes holes for receipt of the cortical screw(s). The compression spring is then inserted into the hip screw-screw plate combination to effect the compression of the fracture.

The patent literature also includes disclosures of bone fixation devices for fixation of proximal femoral fractures. Examples of such prior art devices are shown in U.S. Pat. No. 8,262,709 (Powlan) and U.S. Pat. No. 6,695,844 (Bramlet et al.) and in European Patent App. No. EP 1379186.

While the aforementioned prior art devices appear generally suitable for their intended purposes they nevertheless leave something desired from various standpoints. Accordingly, a need exists for a device that overcomes the disadvantages of the prior art. The subject invention addresses that need.

SUMMARY OF THE INVENTION

In accordance with one aspect of the invention there is provided a bone fixation device for introduction into an angularly extending bore in the femur of a patient to repair a fracture of the proximal femur. The bone fixation device basically comprises a jack tube, a compression screw and a nail.

The jack tube is arranged to be located within the bore in the femur and comprises an elongated tubular member having a central longitudinal axis, a central passageway extending along the central longitudinal axis, and a base plate located at the proximal end of the central passageway. The base plate is arranged to be secured to the femur by a cancellous screw and at least one cortical screw and has an opening in communication with the central passageway. The tubular member has a distal end from which a rod extends in the proximal direction centered on the central longitudinal axis. The rod has external threads and a central canal extending through it centered on the central longitudinal axis. The jack tube additionally comprises at least one elongated slot extending parallel to the central longitudinal axis along at least a portion of the length of the jack tube from the opening in the base plate.

The nail comprises a tubular member having at least one linear blade extending outward therefrom along a substantial portion of the length of the nail.

The compression screw comprises a tubular member having internal threads and is arranged to be disposed within the nail to form a slidable unit.

The slidable unit is arranged to be disposed within the passageway in the jack tube with the at least one blade of the nail being located in the at least one slot in the jack tube and with the internal threads of the compression screw engaging the external threads of the rod, whereupon rotation of the compression screw in a first rotational direction causes the slidable unit to move in the distal direction down the passageway in the jack tube, whereupon the blade cuts into contiguous portions of the femur as the slidable unit moves through the jack tube, thereby preventing the rotation of the nail assembly in the bore in the femur.

In accordance with one preferred aspect of the invention the nail includes a distal end having at least one spike projecting outward therefrom parallel to the central longitudinal axis. The slidable unit is arranged to be slid through the passageway in the jack tube to a fully extended, distally located position wherein the at least one spike extends out an opening in the distal end of the jack tube and into contiguous portions of the femur to anchor the jack tube in the bore in the femur.

In accordance with another preferred aspect of the invention the compression screw is arranged to be rotated in a second and opposite rotational direction after the slidable unit has been moved to the fully extended, distally located position, whereupon the compression screw is retracted slightly with respect to the nail and the jack tube. This action enables the patient to experience dynamization when weight-bearing on the femur, with such dynamization resulting from micro-movement of the nail along the central longitudinal axis while the at least one blade prevents rotation of the nail with respect to the central longitudinal axis.

DESCRIPTION OF THE DRAWING

FIG. 1 is a FIG. 1 a posterior elevational posterior cross section through the proximal portion of a fractured femur of a patient having a bone fixation device constructed in accordance with one exemplary embodiment of the invention positioned therein for facilitating dynamization and concomitant healing of the fracture;

FIG. 2 is a longitudinal sectional view of one component, i.e., the jack tube, of the exemplary embodiment of the bone fixation device shown in FIG. 1;

FIG. 3 is a proximal end view of the jack tube taken along line 3-3 of FIG. 2;

FIG. 4 is a transverse sectional view of the jack tube taken along line 4-4 of FIG. 1;

FIG. 5 is a distal end view of the jack tube taken along line 5-5 of FIG. 1;

FIG. 6 is a top (superior) elevational view of the distal end portion of the jack tube taken along line 6-6 of FIG. 2;

FIG. 7 is a longitudinal sectional view of another component, i.e., the compression screw, of the exemplary embodiment of the bone fixation device shown in FIG. 1;

FIG. 8 is a proximal end view of the compression screw shown in FIG. 7;

FIG. 9 is a transverse sectional view taken along line 9-9 of FIG. 7;

FIG. 10 is a longitudinal sectional view of another component, i.e., the nail, of the exemplary embodiment of the bone fixation device shown in FIG. 1;

FIG. 11 is a distal end view taken along line 11-11 of FIG. 10;

FIG. 12 is a longitudinal sectional view showing the bone fixation device of FIG. 1 with the compression screw and the nail in their maximum distally extended position within the jack tube;

FIG. 13 is a distal end view taken along line 13-13 of FIG. 12; and

FIG. 14 is longitudinal cross section view of the bone fixation device itself in the same state as shown in FIG. 1 where the compression spring has been backed-off (i.e., slightly retracted with respect to the jack tube) leaving the jack tube in place, but with the nail being free for linear micro-movement to achieve dynamization.

DETAILED DESCRIPTION OF THE PREFERRED EMBODIMENT

Referring now to the various figures of the drawing wherein like reference characters refer to like parts, there is shown in FIG. 1 at 20 a bone fixation device constructed in accordance with one exemplary embodiment of this invention.

The bone fixation device 20 basically comprises a jack tube 22 (FIGS. 1 and 2), a compression screw 24 (FIGS. 1 and 6) and a nail 26 (FIGS. 1 and 9). The jack tube is arranged to be located within a bore 12 formed in the femur 10 at the situs of the fracture 14. The bore is formed in a conventional manner, e.g., a guide-wire (not shown) is inserted into the bone along the path for the bore and then a conventional reamer (not shown) is extended along the guide wire to ream out the bore.

As best seen in FIG. 2, the jack tube 22 basically comprises an elongated tubular member having a central longitudinal axis 28, a circular side wall 30, a proximally located base plate 32, a distally located end wall 34, a hollow interior passageway 36, and an elongated externally threaded hollow rod 38 extending within the passageway 36 from distal end wall 34 to a point adjacent the base plate 32. The hollow rod 38 is centered on the central longitudinal axis 28.

The base plate 32 is best seen in FIGS. 2 and 3 and basically comprises a generally planar member which extends at an acute angle to the central, longitudinal axis 28. The base plate includes a large opening 40 in communication with the proximal end of the passageway 36. The upper or superior portion of the base plate includes a tab 42 extending at an angle to the rest of the base plate so that the tab is generally perpendicular to the central, longitudinal axis. The tab includes a hole 44 for receipt of a cancellous screw 46. The cancellous screw 46 serves to fixedly secure the base plate to the tensile trabeculae of the femur. In particular, when the cancellous screw is in place extending through hole 44 in the tab, the screw extends parallel to the central longitudinal axis of the bone fixation device 20 into the tensile trabeculae. The base plate also includes four additional holes, 48A, 48B, 48C and 48D, each adapted to receive a respective cortical screw 50. Each cortical screw is arranged to be extended through its respective hole in the base plate and into the bone of the femur below the fracture so that each screw is approximately perpendicular to the longitudinal axis LAF of the femur as best seen in FIG. 1.

As best seen in FIG. 3, the portion of the base plate 32 contiguous with the opening 40 includes four notches 52A, 52B, 52C and 52D. Each notch is in communication with the proximal end of a respective longitudinally extending slot in the side wall 30 of the jack tube 22. In particular, as best seen in FIGS. 4 and 6 the superior portion of the jack tube's side wall 30 includes a pair of slots 54A and 54B extending down the length of the side wall from just slightly proximally, e.g., 1 cm, of the distal end wall 34 to the base plate 32 at which they meet with the notches 52A and 52B, respectively. In a similar manner, the inferior portion of the side wall 30 includes a pair of slots 54C and 54D extending down the length of the side wall to from just slightly proximally, e.g., 1 cm, of the distal end wall 34 to the base plate at which they meet with the notches 52C and 52D, respectively. The slots and associated notches are arranged to receive respective ones of elongated blades (to be described later) extending outward from the outer surface of the nail and along a substantial length of the nail parallel to the central longitudinal axis 28.

As best seen in FIGS. 2 and 5 the end wall 34 includes four apertures 34A, 34B, 34C and 34D in communication with the central passageway 36 in the jack tube. These apertures serve to enable respective spikes (to be described later) forming a portion of the nail 26 to anchor the device in place.

As mentioned above the tubular rod 38 extends down the central passageway of the jack tube centered on the central longitudinal axis. The rod is externally threaded by helical threads 56 and includes a central, smooth bore or canal 58 extending its entire length. The distal end of the canal 58 is open at the distal end wall 34 of the jack tube. The canal 58 is arranged to receive an elongated wire spike forming a portion of the compression screw 24.

Turning now to FIGS. 7-9, the details of the compression screw 24 will now be discussed. To that end, as can be seen the compression screw is a cylindrical, tubular member having a circular side wall 60 which is internally threaded with helical threads 62. The proximal end of the compression screw 24 is in the faun of an enlarged "Philips" head 64 having cross-slots 66 (FIG. 8). An elongated central wire spike 68 extends down the central axis of the side wall 60 and has a pointed tip 70 which terminates beyond the distal, open end 72 of the side wall. The space within the side wall between the spike 68 and the internal threads 62 is annular in shape and arranged to receive the externally threaded rod 38 of the jack tube, as will be described later.

Turning now to FIGS. 10 and 11, the details of the nail 26 will now be discussed. To that end, as can be seen the nail is a cylindrical, tubular member having a circular side wall 76 whose inner surface is smooth to form a central passageway 78 for receipt of the tubular side wall 60 of the compression spring (as will be described later). Four elongated linear blades 80A, 80B, 80C and 80D extend outward from the outer surface of the side wall 76, with each blade extending from the proximal end 82 of the side wall to a point just slightly proximal, e.g., 1 cm, of the distal end 84 of the side wall. Each blade thus runs parallel to the central longitudinal axis of the nail. The blades are oriented so that the two superior blades 80A and 80B are arranged to be disposed within the superior slots 54A and 54B, respectively (FIG. 6), of the jack tube. In a similar manner, the two inferior blades 80C and 80D are arranged to be disposed within the inferior slots 54C and 54D, respectively, of the jack tube. Four elongated slightly tapered, sharp spikes 86 project outward from the distal end 84 of the side wall 76 and are equidistantly spaced from one another as best seen in FIG. 11.

As mentioned above the compression screw 24 is arranged to be received within the nail 26. In particular, the side wall portion 60 of the compression screw is arranged to be located within the smooth passageway 78 in the nail, with the inner or distal surface of the compression screw's head 64 abutting the proximal end 82 of the nail. When so disposed the compression screw and nail together to form a slidable unit arranged to be slidably disposed with the jack tube after the jack tube has been placed in the bore in the femur (an action which will be described later).

The coupling of the slidable compression screw/nail unit to the in-place jack tube is accomplished as follows: the distal end of the compression screw-nail unit is introduced through the opening 40 in the base plate 28 of the jack tube, with the blades 80A, 80B, 80C and 80D aligned with the notches 52A, 52B, 52C and 52D, respectively, until the internal threads 62 on the compression screw engage the external threads 56 on the threaded rod 38 of the jack tube. At that time the compression screw is rotated in the clockwise direction about its longitudinal axis by a cross-slotted (Philips) driver (not shown), whereupon those threads engage each other thereby moving the screw down the annular portion of the passageway 36 toward the distal end of the jack tube. Since the head 64 of the compression screw is in abutment with the proximal end of the nail, the movement of the screw pushes the nail along with it down the passageway in the jack tube, whereupon the pointed free, distal ends of the four spikes 86 exit through apertures 34A, 34B, 34C and 34D in the end wall 34 of the jack tube. In a similar manner the pointed free, distal end 70 of the central wire spike 68 exits through the open distal end of the canal 58.

Moreover, the movement of the nail 26 in the distal direction down the passageway in the jack tube causes the projecting blades 80A, 80B, 80C and 80D, which extend out through the slots 54A, 54B, 54C and 54D, respectively, to cut a linear path through the bone contiguous with the outer surface of the jack tube in a direction parallel to the central longitudinal axis 28. This action prevents the bone fixation device 20 from rotating within the bore in the femur during the sliding of the compression screw/nail unit through the jack tube. When the distal end of the compression screw/nail unit reaches the inner surface of the end wall 34 of the jack tube, as shown in FIG. 12, the plural spikes 86 and the central wire spike 68 will have dug into the femur to their maximum depth thereby anchoring the nail in place and compressing the fracture line. At this point the compression screw 24 may be rotated in a counter-clockwise direction to retract it slightly from the position shown in FIG. 12 to the position shown in FIGS. 14 and 1, as will be described shortly.

The implantation and use of the bone fixation device 20 to repair a fracture in the proximal femur, like that shown in FIG. 1, will now be described. A conventional guide-wire (not shown) is inserted into the patient through the fracture site. In particular, the guide-wire is inserted in the normal manner so that it extends into the femur head so that its distal end is located just up to the hip joint line. At this time the surgeon should be sure that that the guide-wire is central in the head and neck both in the anterior-posterior and lateral views, as is conventional. After the guide wire is in place a reamer or drill is provided over the guide wire to create a bore about the guide wire. Care should be taken to make sure that the reamer stops approximately 2 cm away from the hip joint. The length of the bore is approximately 90 mm and 2 cm from the distal end of the femur head. This creates a bore similar in size to the outer diameter of the jack tube 22 so that the jack tube can fit within it. The drill is then removed, leaving the guide wire in place to serve as a guide to insert the jack tube over the guide wire. The jack tube is inserted into the bore so that the base plate 32 of the jack tube is against the outer surface of the femur with the upper hole 44 adjacent the portion of the femur in which the cancellous screw 46 will be inserted and with the portion of the plate 32 bearing the holes 48A-48D being adjacent the portion of the femur where the four cortical screws 50 are to be inserted. At this time the guide-wire is still inside the central canal 58 of the jack tube and is anchored in the cancellous bone of the femur head. The cancellous screw 46 is then inserted into the hole 44 and screwed into the cancellous bone parallel to the side wall and central longitudinal axis of the jack tube so that it is anchored to the tensile trabeculae of the femur. The four cortical screws are then extended through their respective openings 48A-48D and screwed into the underlying bone perpendicular to the portion of the base plate where the holes are located so that they are generally perpendicular to the longitudinal axis of the femur, with those screws being anchored in both cortices and the calcar. As is known the to calcar (the main compressive trabeculae) is transfixed by the cortical screws. This portion is the hardest portion of the femur.

The compression screw/nail unit is then introduced into the open end, i.e., the opening 40, of the jack tube 22 until the internal threads 62 on the compression screw meet the external threads 56 on the threaded rod portion 38 of the jack tube as described above, whereupon the compression screw/nail unit moves in the distal direction down the hollow interior of the jack tube. As the compression screw/nail unit moves down the jack tube the blades 80A-80D projecting out of the longitudinally extending slots 54A-54D, respectively, will be press fit into the bone surrounding the jack tube. When the distal end of the compression screw/nail unit reaches the distal end wall 34 of the jack tube the spikes projecting out of the distal end of the nail pass through respective openings in the distal end wall of the jack tube so that they emerge therefrom and become press fit into the bone. At the end of clockwise rotation of the compression screw the nail will be in its fully extended position within the jack tube like shown in FIG. 12 wherein the blades 80A-80D will be press fit within the surrounding bone, with the four spikes 86 and central wire spike 68 transfixed in the cancellous bone of the femur head so that the fracture line is compressed.

A significant feature of the bone fixation device of this invention is that it facilitates dynamization (longitudinal micro-movement) when desired. For example, in case of trochanteric fracture, after the fracture line is compressed and the fracture fixed as just described, the compression screw 24 can then be rotated in the counterclockwise direction, thereby retracting it backward (proximally) a short distance, e.g., approximately 0.5 cm, from the nail 26. The nail will not be allowed to retract because its blades and spikes are press fit inside the cancellous bone. At this time weight bearing on the femur by the patient will compress the nail by compressing the spikes and blades, while the jack tube is not allowed to move because its base plate 32 is fixed to the femur by the cancellous screw 46 and cortical screws 50. In short, the patient's weight bearing will compress the nail against the jack tube so that dynamization can occur, which further compresses the fracture site. As is known dynamization is a highly selective mechanism and is able to occur because the fixation device 20 allows longitudinal movement but prevents rotational movement, i.e., the longitudinally extending blades of the nail are confined in the longitudinally extending slots in the jack tube, plus the cancellous screw acts as an anti-rotation screw. In this regard, while there is a connection between the jack tube and the compression screw by their mating threads the nail is not connected to either the jack tube or compression screw so that it can move independently by pushing forward by the compression screw's head and backward by weight-bearing of the patient.

Another important feature of this invention is the fact that the screws at the base plate of the jack tube are divided into two groups, namely, the cancellous screw (which is extended parallel to the longitudinal axis of the jack tube) and the cortical screws (which are perpendicular to the base plate and to the longitudinal axis of the femur and thus diverge with respect to the longitudinal axis of the jack tube).

In accordance with one exemplary embodiment of this invention, the cancellous screw 46 is selected so that it extends approximately 6.5 mm into the main tensile trabeculae, and the four cortical screws are selected so that they each extend approximately 4.5 mm into the femur. The outside diameter of the jack tube's side wall 30 is approximately 13.5 mm and is approximately 7 cm long at its upper portion and 8 cm long at its lower portion, i.e., the portion adjacent the cortical screws. The diameter of the central passageway 36 in the jack tube is approximately 11.5 mm. The aforementioned dimensions are merely exemplary and other sizes of the various components of the device 20 are contemplated. Moreover, the number of blades and/or spikes used is also, exemplary, so that more or less than the number of blades and spikes shown and described above may be used.

As mentioned earlier, the anterior or distal end of the nail 26 does not include any blades for approximately the first 1 cm of its length. The reason for this is to facilitate the entrance of the nail into the jack tube until the engagement of the threads on the compression screw with the threads on the jack tube become strong enough to drive the blades into the surrounding bone as the compression screw/nail unit is extended into the jack tube.

As should be appreciated from the foregoing the bone fixation device of the subject invention and its technique of fixation results in a very strong repair of a fracture in the proximal portion of the femur and has various advantages over the prior art. In particular, the DHS system mentioned above merely uses two points of fixation. In contradistinction the subject invention provides three fixation points. The first point is inferior to the jack tube and is formed by the cortical screws which are anchored in the calcar. The second point is the cancellous screw located above the jack tube which is anchored to the main tensile trabeculae. The third point is the accessory fixation at the femoral head by the spikes of the nail and the central wire spike of the compression screw which is press fit the cancellous bone of the femoral head. In addition, there is direct anchoring of the main tensile and main compressive trabeculae of the neck of the femur. The prior art DHS system doesn't become anchored to both trabeculae. Also, there is direct fixation of the fracture line, or at least very near the fracture site. In the case of the DHS system, the fixation is further away from the fracture site. In addition, there is less muscle dissection in using the subject invention because the jack plate is rather short. This means there is should be faster healing of bone fracture, which depends on the integrity of the surrounding vascular soft tissues, i.e., the integrity of the muscles surrounding the fracture accelerates healing of the fracture. The subject invention also enables less time consumption in dissection and re-suturing of the muscles. Further still, there is less blood loss from muscle dissection because cutting the muscles to apply a long plate like that of the DHS system is typically associated with significant blood loss which is critical especially for elderly patients who are highly liable to these types of fractures due to osteoporosis.

While the blades of the nail of this invention prevent rotation they do allow dynamization with weight bearing, which means the highest degree of selectivity to prevent unwanted movements, i.e., the rotation. Moreover, the cancellous bone of the femur head is preserved to a very large extent because it is transfixed by the spikes of the compression screw which prevent the rotation but allow dynamization, thereby preserving the bone substance of the head. The current technique of using the DHS system entails removal of a large amount of cancellous bone in the femoral head and that bone is replaced by the head of the DHS screw. This action increases the chances of avascular necrosis. In this regard, recent studies show that the DHS system has higher incidence of avascular necrosis in the fracture neck femur than the prior art's use of cannulated cancellous screw fixation as a result of the increase in the pressure in the femoral head by the large size head of the DHS screw. However, cannulated screws, which are a desirable method of fixation for a fracture at the femur neck, are weak and become more liable to fracture because they are hollow. Further, cannulated screws are somewhat difficult to apply because the proper application requires that they be generally parallel to each other in the two planes, namely, anteroposterior, and lateral. Therefore, the subject invention offers advantages over the prior art since it is very strong, plus it serves to preserve cancellous bone mass at the head of the femur. In short, the subject invention provides advantages over the prior art DHS system and the prior art use of cannulated screw and addresses their complications.

In addition to the above, the bone fixation device of this invention is more appealing from an aesthetic point of view, e.g., the small base plate allows one to make a smaller incision, which is cosmetically more acceptable and has faster healing.

Moreover, stresses are evenly distributed throughout the jack tube and the ridges because they are the same size. Thus, there is little possibility of stress to be concentrated at certain points. The distribution of stress inherent in the use of the subject invention is more physiologically beneficial and promotes healing. In contradistinction, with use of the DHS system, stresses are concentrated on the head of the DHS screw and on its contact with the barrel.

In the exemplary embodiment of the device described above the jack tube and the longitudinally extending blades of the nail are each of constant diameter along the entire length of the assembly. The blades serve to increase the bone-metal surface contact by effectively increasing the circumference of the jack tube. This increase in bone-metal surface contact biomechanically means faster healing. Thus, the invention is very suitable biomechanically to the anatomy of the femoral neck. Because the femoral neck is not a regular circle, but is more or less elliptical in shape. The antero-postero diameter (average of 2.5 cm) is shorter than the supero-inferior diameter (average of 3.5 cm or more). At the same time the subject invention is larger from a supero-inferior direction because the ridges and the cancellous screw are in the supero-inferior direction. Thus, the subject invention is more or less elliptical in shape matching the irregular anatomy of the femoral neck which precisely helps in distribution of stresses according to anatomical parameters of the femoral neck. Clinically this can mean faster healing by matching the stress distribution to the anatomy.

Without further elaboration the foregoing will so fully illustrate our invention that others may, by applying current or future knowledge, adopt the same for use under various conditions of service.

We claim:

1. A bone fixation device for introduction into an angularly extending bore in the femur of a patient to repair a fracture of the proximal femur, said device comprising a jack tube, a compression screw and a nail, said jack tube being configured to be located within the bore in the femur and comprising an elongated tubular member having a central longitudinal axis, a side wall, a central passageway extending through said side wall and along said central longitudinal axis, a base plate located at a proximal end of said central passageway, said base plate being configured to be secured to the femur by a cancellous screw and at least one cortical screw and having an opening in communication with said central passageway, said tubular member having a distal end to which a rod is fixedly secured and from which said rod extends in the proximal direction centered on said central longitudinal axis, said rod having external threads and a central canal extending through said rod centered on said central longitudinal axis, said jack tube additionally comprising at least one elongated slot extending through said side wall parallel to said central longitudinal axis along at least a portion of the length of said jack tube from said opening in said base plate, said nail comprising a tubular member having at least one linear blade extending outward therefrom along a substantial portion of the length of said nail, said compression screw comprising a tubular member having internal threads and being configured to be disposed within said nail to form a slidable unit, said slidable unit being configured to be disposed within said passageway in said jack tube with said at least one blade of said nail extending radially outward through said at least one slot in said jack tube so that a portion of said at least one blade extends out of said slot and with said internal threads of said compression screw engaging said external threads of said rod, whereupon rotation of said compression screw in a first rotational direction causes said slidable unit to move in the distal direction down said passageway in said jack tube, whereupon said portion of said at least one blade cuts into contiguous portions of the femur as said slidable unit moves through said jack tube, thereby preventing the rotation of said bone fixation device in said bore in the femur.

2. The bone fixation device of claim 1, wherein said nail includes a distal end having at least one spike projecting outward therefrom parallel to the central longitudinal axis and said slidable unit is configured to be slid through said passageway in said jack tube to a fully extended, distally located position wherein said at least one spike extends out an opening in said distal end of said jack tube and into contiguous portions of the femur to anchor said jack tube in the bore in the femur.

3. The bone fixation device of claim 2, wherein said compression screw is configured to be rotated in a second and opposite rotational direction after said slidable unit has been moved to said fully extended, distally located position, whereupon said compression screw is retracted slightly with respect to said nail and said jack tube, thereby enabling micro-movement of said nail along the central longitudinal axis while said at least one blade prevents rotation of said nail with respect to said central longitudinal axis to facilitate dynamization when the patient is weight-bearing on the femur.

4. The bone fixation device of claim 1, wherein the bore in the femur is configured to have an elongated guide-wire extended through it, wherein said canal in said rod is configured to receive said guide-wire to enable said jack tube to be located in the bore in the femur at a desired position, and wherein said bone fixation device is configured to enable the guide-wire to be withdrawn from the bore in the femur through said canal after said jack tube is in said desired position.

5. The bone fixation device of claim 1, wherein said nail includes four blades, two blades being located superiorly and two blades being located inferiorly, and wherein said jack tube includes four slots, each of said slots being configured to receive a respective one of said blades of said nail, whereupon said superiorly located blades extend along said jack tube on either side and equally spaced from the cancellous screw and wherein said inferiorly located blades extend along said jack tube on either side and equally spaced from the at least one cortical screw.

6. The bone fixation device of claim 2, wherein said nail includes four blades, two blades being located superiorly and two blades being located inferiorly, and wherein said jack tube includes four slots, each of said slots being configured to receive a respective one of said blades of said nail, whereupon said superiorly located blades extend along said jack tube on either side and equally spaced from the cancellous screw and wherein said inferiorly located blades extend along said jack tube on either side and equally spaced from the at least one cortical screw.

7. The bone fixation device of claim 6, wherein said nail includes four peripheral spikes disposed at equidistantly spaced locations about the distal end of said nail and one central spike centered on said central longitudinal axis.

8. The bone fixation device of claim 1, wherein said base plate is a somewhat planar member extending at an acute angle to said central longitudinal axis.

9. The bone fixation device of claim 8, wherein said base plate includes a tab portion extending at an acute angle to said base plate and having a hole therein for receipt of the cancellous screw, whereupon the cancellous screw extends into the femur generally parallel to said central longitudinal axis.

10. The bone fixation device of claim 9, wherein said base plate includes a hole therein for receipt of said at least one cortical screw, whereupon the at least one cortical screw extends into the femur at an obtuse angle with respect to said central longitudinal axis and generally perpendicular to the longitudinal axis of the femur.

11. The bone fixation device of claim 10, wherein said bone fixation device additionally comprises a cancellous screw and four cortical screws.

12. The bone fixation device of claim 8, wherein the length of said jack tube measured from the base plate to the distal end of the jack tube along the inferior side thereof is approximately 8 cm, the length of the jack tube measured from the base plate to the distal end of the jack tube along the superior side thereof is approximately 7 cm, the outside diameter of the jack tube is approximately 13.5 mm, and the inside diameter of the passageway in the jack tube is approximately 11.5 mm.

13. The bone fixation device of claim 12, wherein the inside diameter of said canal in said rod is approximately 3.5 mm.

14. The bone fixation device of claim 12, wherein said compression screw comprises an enlarged head and wherein the length of said compression screw from said enlarged head to said distal end is approximately 7 cm, the outside diameter of said compression screw from said enlarged head to said distal end is approximately of 8.5 mm.

15. The bone fixation device of claim 13, wherein the length of said head of said compression screw is approximately 0.5 cm and with an outside diameter of approximately of 11.5 mm.

16. The bone fixation device of claim 14, wherein said inside diameter of said nail is approximately 8.5 mm.

* * * * *